United States Patent
Lim et al.

(10) Patent No.: US 10,064,720 B2
(45) Date of Patent: Sep. 4, 2018

(54) SET COMPRISING AN APPARATUS AND A MEDICAL IMPLANT

(71) Applicant: VENUS MEDTECH (HANGZHOU), INC., Hangzhou (CN)

(72) Inventors: Hou-Sen Lim, Singapore (SG); Wolfgang Goetz, Regensburg (DE)

(73) Assignee: VENUS MEDTECH (HANGZHOU), INC., Hangzhou (CN)

(*) Notice: Subject to any disclaimer, the term of this patent is extended or adjusted under 35 U.S.C. 154(b) by 291 days.

(21) Appl. No.: 14/902,570

(22) PCT Filed: Jul. 16, 2014

(86) PCT No.: PCT/EP2014/065292
§ 371 (c)(1),
(2) Date: Jan. 2, 2016

(87) PCT Pub. No.: WO2015/007793
PCT Pub. Date: Jan. 22, 2015

(65) Prior Publication Data
US 2016/0166383 A1    Jun. 16, 2016

(30) Foreign Application Priority Data
Jul. 16, 2013 (EP) ..................... 13176671

(51) Int. Cl.
*A61F 2/24* (2006.01)
*A61F 2/95* (2013.01)

(52) U.S. Cl.
CPC .............. *A61F 2/2439* (2013.01); *A61F 2/95* (2013.01); *A61F 2002/9511* (2013.01)

(58) Field of Classification Search
CPC ... A61F 2/2439; A61F 2/95; A61F 2002/9511
See application file for complete search history.

(56) References Cited

U.S. PATENT DOCUMENTS

| 8,157,853 B2 * | 4/2012 | Laske .................. A61F 2/2412 623/1.11 |
| 2006/0235509 A1 | 10/2006 | Lafontaine |
| 2009/0192585 A1 | 7/2009 | Bloom et al. |
| 2011/0040366 A1 | 2/2011 | Goetz et al. |

FOREIGN PATENT DOCUMENTS

| WO | 2008/029296 A2 | 3/2008 |
| WO | 2012/084178 A2 | 6/2012 |

OTHER PUBLICATIONS

PCT/EP2014/065292, International Search Report, dated Oct. 2, 2014.

* cited by examiner

*Primary Examiner* — Julian W Woo
(74) *Attorney, Agent, or Firm* — Hamre, Schumann, Mueller & Larson, P.C.

(57) ABSTRACT

The present invention relates to set comprising an apparatus (100) for folding or unfolding at least one medical implant (300) by means of at least one tension thread (11, 11'), wherein the apparatus (100) comprises a shaft (1) and a tensioning device for altering a form or shape of the foldable and/or unfoldable implant (300) by means of the tension thread (11, 11'). In at least one shaft section thereof, the shaft (1) comprises a plurality of individual shaft fibers (13).

20 Claims, 8 Drawing Sheets

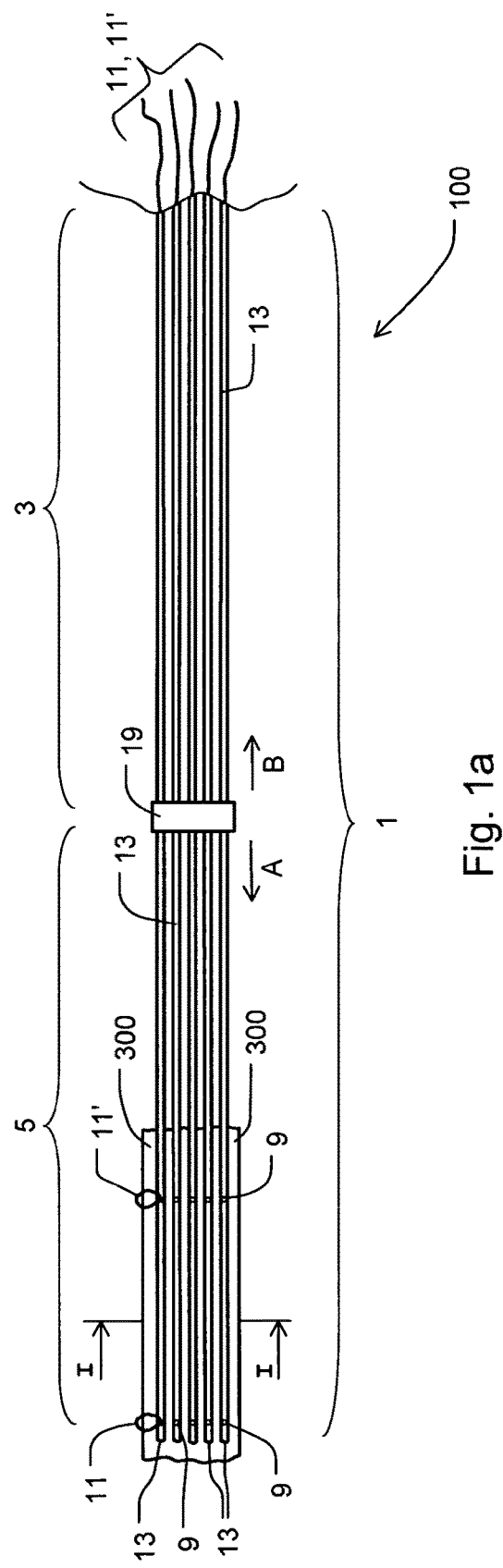
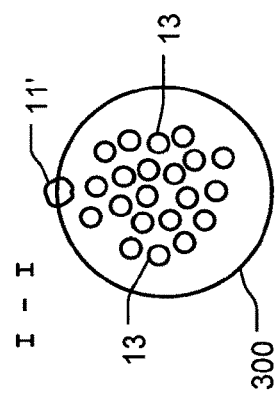

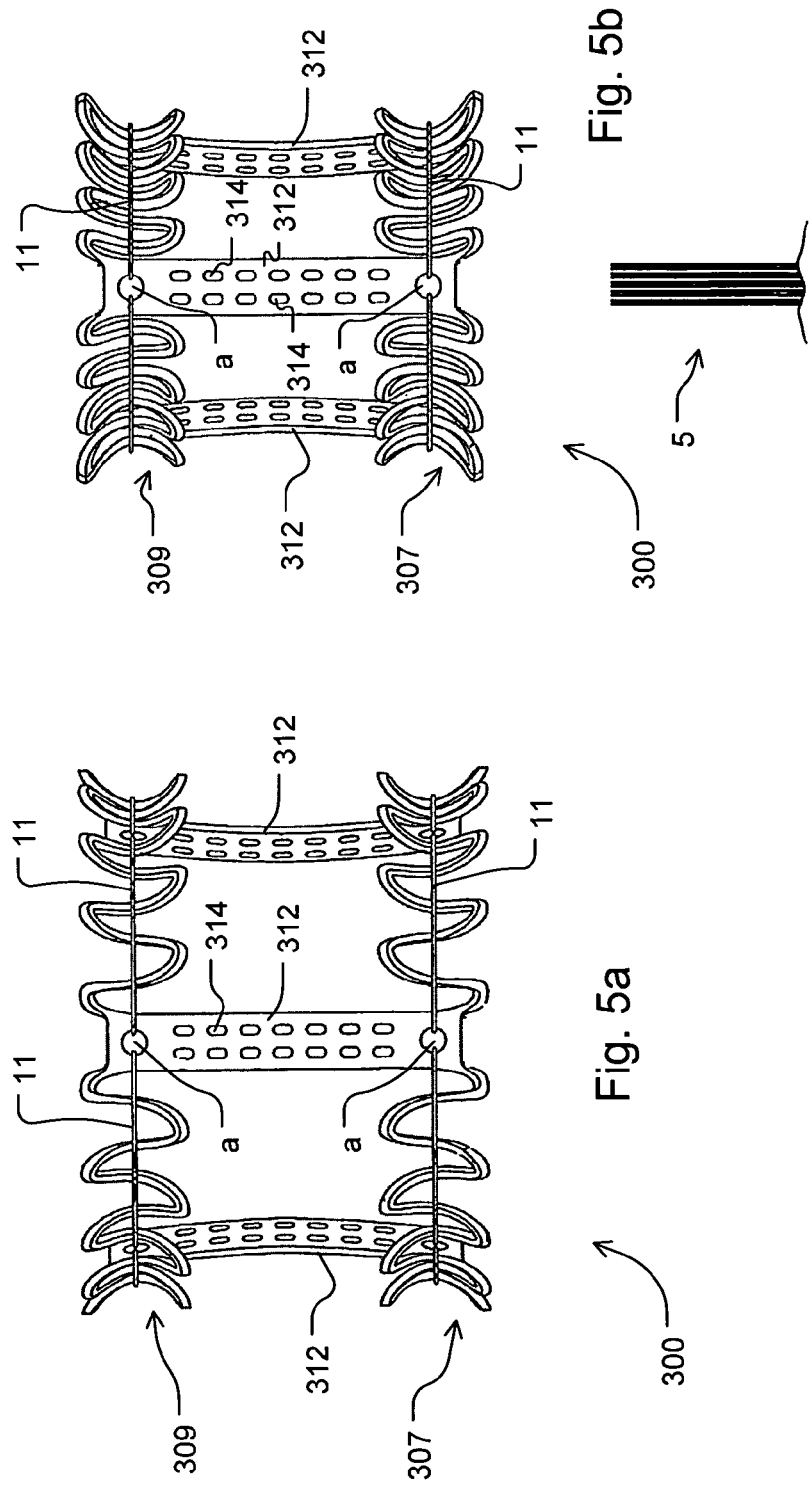

SET COMPRISING AN APPARATUS AND A MEDICAL IMPLANT

The present invention relates to a set for folding or unfolding an implant.

From practice, implants are known that can be folded and/or unfolded by means of one or more threads transferring tension onto the implant. Furthermore, respective apparatuses for folding and unfolding are known from practice.

One object of the present invention is to propose a further set having an apparatus for folding or unfolding a foldable and/or unfoldable implant by means of a tension thread.

This object is solved by means of a set having the features herein described.

Thus, according to the present invention, a set is proposed having an implant and an apparatus for inserting and/or folding and/or unfolding the implant by means of at least one tension thread. The apparatus comprises a shaft.

Furthermore, the apparatus comprises at least one tensioning device for altering a form or shape, a geometry or a folding state of the foldable and/or unfoldable implant by means of the at least one tension thread.

The set further comprises at least one implant connected with tension threads for the purpose of folding and/or unfolding or provided or prepared for being connected with tension threads.

The shaft of the apparatus comprises in at least one shaft section thereof a plurality of individual shaft fibers.

Further, some or all of the individual shaft fibers have each at least one shaft opening for passing through the tension threads.

The implant comprises apertures through which tension threads are guided or passed.

Tension threads which pass through (i.e., enter into or exit from) one particular (or many) of the shaft openings of a particular individual shaft fiber also pass together through (i.e., enter into or exit from) a common aperture of the implant.

Advantageous embodiments or developments of the set according to the present invention are each subject matter of the dependent claims.

Embodiments according to the present invention may each comprise one or more of the following features in any arbitrary combination.

In some embodiments of the set according to the present invention, altering a form or shape of the implant means reducing or increasing a diameter, in particular an outer diameter, of the implant. Alterations of the diameter may be accompanied by any kind of alteration of the implant's length or any other alteration, or may be not.

In certain embodiments according to the present invention, folding the implant means reducing the implant's diameter.

In some embodiments according to the present invention, folding is to be understood as increasing a diameter of the implant.

In certain embodiments according to the present invention, unfolding means the opposite of folding.

In some embodiments according to the present invention, a common aperture is to be understood as a single aperture through which more than one tension thread are commonly guided or passed through. However, in other embodiments according to the invention, a common aperture means a particular site where a pair of tension threads are guided through the circumference of the implant. That common aperture may be subdivided into two or more sub-apertures which, however, all belong to a functionally 'common' passage through the shaft, wall, envelope or circumference of the implant. Two or more sub-apertures may even then be referred to as a common aperture within the sense of the present invention, as long as an angle formed between the pair of tension threads is not substantially changed by the fact the common aperture is comprised by not by one but by a multitude of apertures.

In certain embodiments according to the present invention, the term 'one (particular) common aperture' encompasses all apertures that are arranged on one (particular) post or strut, in particular at one and the same spot (of the implant, e. g.) or in either a proximal or distal section thereof.

In some embodiments according to the present invention, one or each of the common apertures are provided in one or more posts or struts of the implant which extends in parallel to a longitudinal axis of the implant (e. g. in an unfolded or folded state outside of the body).

In certain embodiments according to the present invention, all of the common apertures are provided only in such posts or struts of the implant.

In some embodiments according to the present invention, the posts or struts are arranged to connect a distal ring-shaped element of the implant with a proximal ring-shaped element thereof. The posts or struts may be arranged to maintain a distance or an unchangeable distance between the distal and the proximal ring-shaped elements.

In certain embodiments according to the present invention, the at least one opening of the shaft fiber is an opening in the end face of the shaft fiber.

In some embodiments according to the present invention, the at least one opening of the shaft fiber is an opening in the shaft or circumference or envelope of the shaft fiber.

In certain embodiments of the set according to the present invention, the shaft openings of the shaft fibers and the apertures of the implant are matched such that tension threads which pass through one or more shaft opening(s) and which also pass together through a common aperture do not—or not substantially—change the angle between them during folding and/or unfolding.

In some embodiments according to the present invention, the implant, shaft fibers and pairs of tension threads are arranged such that in an area of the shaft openings the respective tension threads (or sections thereof) belonging to one pair of tension threads do not diverge upon folding and/or unfolding the implant.

In particular embodiments according to the present invention, the tension threads which pass through one or more shaft opening(s) of a particular individual shaft fiber and which also pass together through a common aperture of the implant are guided in parallel or more or less in parallel (in at least one projection or in one plane) between shaft opening and aperture. Preferably, they are guided such that even upon folding or unfolding of the implant, the pair of tension threads do remain parallel or substantially parallel (or the angle between does not change or not substantially change).

In certain embodiments according to the present invention, the implant's diameter is present in a plane perpendicular to a main flow direction of the implant, in case the implant is flown through by a fluid after its implantation.

In some embodiments of the set according to the present invention, the at least one tension thread is a thread or filament or yarn, respectively. It can be designed or embodied similar to a surgical sutural thread or it can be such a surgical sutural thread. It can be designed or embodied as a rope or a cord or twine or string, respectively. It can be designed or embodied as a chain comprising a plurality of chain members engaged with adjacent chain members.

In the following, whenever reference is made to a thread or tension thread, the terms may include a plurality of threads or tension threads as well insofar as a person skilled in the art recognizes the exchangeability of the terms.

In certain embodiments, the shaft of the apparatus is in at least one section thereof embodied rigidly. In some embodiments, the shaft of the apparatus is in at least one section thereof embodied such as to be bendable in one or more directions (i. e. it may be bent in a longitudinal direction or in a direction of the shaft's width, in both directions or in any other direction). In some embodiments, the shaft is embodied extendably or stretchably. In other embodiments, the shaft is embodied stiffly or inflexibly.

In one embodiment of the set according to the present invention, during its implanted implantation state, the implant is able to be penetrated by fluids or is permeable for fluids, respectively, in its longitudinal direction. The terms "permeable" or "able to be penetrated" hereby refer to the ability of the implant to be penetrated or flown through by fluids.

In some embodiments of the set according to the present invention, in the moment of unfolding or folding, the implant is loosely arranged or attached to or at or on a receiving area of the apparatus. In some embodiments according to the present invention, the implant is thereby connected with the receiving area only by means of the tension threads.

In certain embodiments of the set according to the present invention, the tension thread comprises or consists of a bundle or a plurality of threads or thread elements.

In some embodiments according to the present invention, a shaft fiber of the apparatus is permeable or patent (like a blood vessel) within its interior in at least sections of its longitudinal direction or along its entire length. In those embodiments, the shaft fiber comprises a wall.

In certain embodiments, at least one of the tension threads (or all of them) is partly arranged within an inner space of the respective shaft fiber and extends from there to an outside of the shaft fiber through the shaft opening.

In some embodiments, at least one of the tension threads (or all of them) exits from an inner space of the shaft fiber through one shaft opening. In other embodiments, at least one of the tension threads (or all of them) exits from the inner space through two or more shaft openings.

In certain embodiments according to the present invention, the at least one shaft opening is provided at or on the front surface of the shaft fiber. In other embodiments according to the present invention, it is arranged at or on a circumferential surface or lateral surface area of the shaft. Preferably, the shaft opening is arranged in or within a tip area of the shaft fiber or in or within a proximal area of the shaft fiber.

In certain embodiments according to the present invention, the shaft fiber comprises a plurality of shaft openings uniformly or non-uniformly distributed or arranged along or about a periphery or along or about a circumferential surface or lateral surface area of the shaft or of the shaft fiber. Additionally or alternatively, the shaft openings may be dispersed along or about a longitudinal direction of the shaft or of the shaft fiber. For example, in some embodiments according to the present invention, shaft fibers may have two or more shaft openings which are arranged under different distances between the respective opening and the tip or one end of the corresponding shaft fiber.

In certain embodiments according to the present invention, at least one or all of the shaft fibers are arranged such that they do no move relatively to the apparatus in a longitudinal direction of the apparatus upon folding or unfolding the medical implant.

In some embodiments according to the present invention, tension threads for folding and/or unfolding the implant enter and/or exit through the shaft opening.

In certain embodiments according to the present invention, during the use of the apparatus, shaft fibers of the plurality of individual shaft fibers are always present in bundled form in at least one first section of the shaft section. In contrast, in a second section, they are provided for moving or drifting away from each other during use of the apparatus.

In some embodiments according to the present invention, the second section is closer to the tip of the apparatus than the first section.

In certain embodiments according to the present invention, the first section directly merges with or passes over into the second section.

In some embodiments according to the present invention, the individual shaft fibers are arranged in contact to each other in the first section such that there is no lumen such as, e. g., a central lumen, for example a lumen usable during the use of the apparatus for fulfilling particular functions, provided between the shaft fibers in the first section.

Spoken differently, the shaft fibers are arranged closely or at close quarters.

In some embodiments according to the present invention, the term "individual shaft fibers"—when used discretely—comprises all shaft fibers present of the plurality of the entirely present individual shaft fibers; in other embodiments, it only comprises some of them.

In certain embodiments according to the present invention, the number of individual shaft fibers is set to two shaft fibers; in other embodiments, the number is set to three, four, five, six, seven etc. The number may be a great number; it may exceed ten or twenty and comprises every natural number up to at least 30 or 40.

A great number of individual shaft fibers advantageously allows for folding and unfolding the implant (for example, the periphery of the implant) which experiences an action by means of the tension threads for folding/unfolding, that exit from the individual shaft fibers into a great number of loops around the circumference of the implant. The inventors of the present invention have recognized that in certain embodiments, this favors a uniform folding or unfolding the implant. Additionally, a great number of shaft fibers may advantageously avoid any buckling or bulging or denting of the periphery.

A great number can be any numerical value between 3 and 40, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40. Greater values are encompassed by the present invention as well.

In some embodiments according to the present invention, neither the individual shaft fibers nor sections thereof are arranged within the interior or material of a wall of an envelope, an outer boundary or limitation, or the like of the apparatus.

In certain embodiments according to the present invention, the individual shaft fibers are provided such that they cannot be shifted or moved relative to the remainder of the apparatus in a longitudinal direction thereof.

In some embodiments according to the present invention, shaft fibers of the plurality of individual shaft fibers each comprise one or more shaft openings. The one or more tension threads can enter into and/or exit from the respective shaft fiber through the shaft openings.

In certain embodiments according to the present invention, such shaft openings are solely provided for allowing tension threads to enter in or into and/or leave or exit from the respective individual shaft fiber.

In some embodiments according to the present invention, the individual shaft fibers are designed or embodied to comprise one or more through-openings (extending into a longitudinal direction of the shaft fiber) or one or more hollow interiors. These through-openings or hollow interiors may allow guiding one or more tension threads through the shaft fiber, e. g. from the tensioning device of the apparatus to a shaft opening or to an exit opening at the tip portion of the shaft fiber.

In some embodiments according to the present invention, the tension threads are arranged within an interior of the shaft fibers such that they can be shifted or moved relative to the respective shaft fibers.

In some embodiments according to the present invention, the individual shaft fibers and/or the tension threads do not comprise any devices for establishing a hook engagement with the implant.

In some embodiments according to the present invention, some or all of the tension threads are connected with the implant by solely entangling or entwining the implant or a part or section or portion thereof.

In certain embodiments according to the present invention, during a state of use of the apparatus, shaft fibers of the plurality of individual shaft fibers are arranged movably in or forth from (in the direction towards the tip of the apparatus) at least the second section of the shaft respectively independently of each other and/or independently of the position of the implant relative to the apparatus for folding or unfolding. Differently spoken, they can move away from each other and/or move towards each other in or within the second section.

In some embodiments according to the present invention, the shaft comprises in at least one section thereof a device for bundling individual shaft fibers of the plurality of individual shaft fibers.

In certain embodiments according to the present invention, there are provided more than just one device for bundling (but two, three, four, and so on, devices of this kind). Additionally or alternatively, in some embodiments, the device for bundling comprises not just one means, e. g. having the shape of a collar, but more than one means (e. g., two, three, four, and so on, means).

In certain of the embodiments comprising more than one device for bundling or means for bundling, the individual devices or means are provided on the shaft fibers while being spaced apart from each other. The particular space or distance chosen or set may advantageously contribute to setting or predetermining the stiffness, bendability and other mechanical features of the shaft fibers. This may be true for the shaft fibers' parts arranged between the devices or means for bundling. It may also be true for the parts of the shaft fibers that are not bundled but allowed to move freely with regard to each other.

In some of the embodiments comprising more than one device for bundling or means for bundling, a (that is, one or more) core element or a (that is, one or more) interconnecting element is provided on, at or within the bundle of shaft fibers. The core element or interconnecting element may also advantageously contribute to setting or predetermining the stiffness, bendability and other mechanical features of the shaft fibers. The core element or interconnecting element may be attached to one, two or all of the devices or means for bundling. However, it may not be attached as well. The core element or interconnecting element may be provided to be extendable and to change its length, for example, when a distance between neighbouring, adjacent or interacting devices for bundling or means for bundling is changed or adapted to need.

Both providing more than only one device for bundling or means for bundling and providing a core element or the like may in certain embodiments of the present invention allow for keeping the shaft fibers in parallel in use along a certain or even predetermined distance. Again, this may also advantageously contribute to setting or predetermining the stiffness, bendability and other mechanical features of the shaft fibers, both in the vicinity of core element or device or means for bundling and also in the second section of the shaft in which the shaft fibers are intended to move, wander or migrate freely in case of need.

In certain embodiments according to the present invention, the device for bundling is designed or embodied as a ring encompassing the individual shaft fibers to be bundled and inhibiting the shaft fibers from drifting or moving away from each other. In some embodiments according to the present invention, the device for bundling is designed or embodied as a clamp, a protrusion or a constriction of the apparatus, or the like.

In certain embodiments according to the present invention, the device for bundling individual shaft fibers is arranged to be shiftable along a longitudinal extension of the apparatus. Additionally or alternatively, the device for bundling may be alterable or manipulatable or engineerable in any other way. For example, the device for bundling may be manipulated by setting or altering a gap or play between shaft fibers and the device for bundling limiting or encircling the shaft fibers. Additionally or alternatively, the device for bundling can be provided for being used at or on different sections of the apparatus along the longitudinal extension thereof. The afore-mentioned manipulations may advantageously alter or adapt to the need, respectively, the stiffness or rigidity of the individual shaft fibers in or within the second section.

In other embodiments, a device for bundling such as specified above is not provided. In some embodiments, it is not possible to distinguish a first section from a second section (such as specified above and below) or required.

In some embodiments according to the present invention, individual shaft fibers are designed or embodied and provided or prepared for moving or bending or tilting, or the like, towards a rim portion of the implant when applying tension onto the implant by means of the tension thread extending through the said individual shaft fiber.

"Moving towards" is in some embodiments to be understood as a deviation of at least one section of the individual shaft fiber (mainly in the second section or in a tip area of the individual shaft fiber) from a position that is arranged closer to a center of a cross section of the apparatus according to the present invention into a position that is arranged more radially as compared to the first position, e. g. into a rim area or towards a rim portion.

In certain embodiments according to the present invention the bundle of shaft fibers can be (or are) arranged in a circular manner.

In some embodiments according to the present invention, the shaft fibers (e. g. nine shaft fibers in total) are arranged in a circular manner in both the unfolded and/or the folded state of the medical implant.

In certain embodiments according to the present invention, a rim portion is a section of a circumference of the implant or a main part thereof, for example the exterior wall or envelope.

In some embodiments according to the present invention, the rim portion comprises a part of the foldable material of the implant. The rim portion may be a curve-shaped part of an outer limitation or of a wall (e. g. a mesh, grid, strut or bar structure) of the implant.

In certain embodiments according to the present invention, tension threads exiting from individual shaft fibers are connected with a rim portion of the implant for applying a force onto the implant.

In some embodiments according to the present invention, the rim portion which is folded or unfolded by means of a particular shaft fiber or by means of the one or more tension threads of the shaft fiber, respectively, is the entire foldable and/or unfoldable periphery of the implant. In those embodiments, the rim portion does not comprise the entire periphery, whereas, in other embodiments, it indeed does.

In certain embodiments according to the present invention, tension threads exiting from individual shaft fibers are connected with a rim portion of the implant for applying a force onto the rim portion. In certain embodiments according to the present invention, tension threads exiting from at least two or more individual shaft fibers are connected with the said rim portion, or parts thereof.

In some embodiments according to the present invention, tension threads exiting from individual shaft fibers are connected with a rim portion in an overlapping manner for applying a force onto the rim portion of the implant. In those embodiments, it is intended to fold or unfold a particular rim portion or a part thereof by means of two, three or more tension threads exiting from different individual shaft fibers. In this way, an overlap of several tension threads is achieved in an area of a particular rim portion. This may advantageously contribute to a more uniform folding of the implant.

In certain embodiments according to the present invention, tension threads exiting from individual shaft fibers are connected with differently large, broad, long or in any other way different rim portions of the implant for applying a force on the said rim portions. Thus, a first rim portion may have a first arc or curve length x, a second rim portion may have a second arc or curve length 2x or x_2, x_2 being different from x. This may advantageously allow for or contribute to a more uniform folding of the implant even in cases in which the implant does not behave in a mechanically uniform way over its entire periphery upon folding.

In some embodiments according to the invention, some or all of the tension threads, i. e. at least one tension thread, do not encompass the whole circumference of the implant. In certain embodiments according to the invention, one or more of the tension threads re-enter the lumen of the implant through apertures provided within the circumference or rim of the implant that are, for example, adjacent to the aperture through which the respective tension thread has exited from the lumen. In some embodiments according to the invention, some or all of the tension threads are provided to re-enter the lumen by an aperture provided in the rim that is different from the aperture through which the particular tension thread has exited from the lumen to an outside of the implant. In particular, any tension thread may re-enter the lumen by the next aperture, the next but one, next but two, next plus three, or the like, on the circumference or on the rim.

Please note that in any embodiment according to the present invention the number of apertures may always be identical to the number of fibers. However, the number of apertures may as well differ from the number of fibers.

In some embodiments according to the present invention, the apparatus is designed or intended for folding and/or unfolding an implant designed as a stent or a heart valve arrangement.

In some embodiments of the present invention, the implant is a stent or a heart valve arrangement.

In certain embodiments of the present invention, individual shaft fibers on the one hand and the implant on the other hand are adapted, chosen or fit to each other as regards their mechanical properties. In certain embodiments according to the present invention, this may be effected such that, during the process of folding the implant, a first force or tension required for moving the shaft fibers in a section thereof, in particular in an area of a shaft opening for tension threads, from their longitudinal alignment or in a direction of the radial extension of the implant is lower than a second force or tension. The second force or tension is a force or tension required for effecting a folding or the beginning or an appreciable beginning of a folding of the implant by means of the tension threads connected with the implant that exit from the shaft openings. Said in a more simple manner, in some of those embodiments, upon application of tension, the individual shaft fiber firstly moves in a—for example, radial—direction towards a rim portion of the implant upon applying tension by means of the tension threads exiting from the shaft fiber, prior to beginning any folding of the respective rim portion. This adaptation or adjustment of properties of the individual shaft fibers (such as bendability, flexibility, elasticity, or rigidity) with respect to the properties of the implant may ensure that, upon applying tension by means of the tensioning device, the individual shaft fibers firstly automatically move into a position in which the force applied or to be applied by means of the tension thread is applied onto the implant or onto the rim portion in or under a desired angle.

In some embodiments according to the present invention of, the implant is connected or intended to be interconnected with the apparatus by means of tension threads such that the tension threads (independently of each other or in an overlapping manner) interconnect with a great number of peripheral sections of the implant. A great number may be any numerical value between 3 and 40, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40. Greater values are encompassed by the present invention as well.

In certain exemplary embodiments according to the present invention, at least one of the apparatus and the implant comprises exclusively, i.e. only, (one or more) materials that are MRI (short for: magnetic resonance imaging) compatible. In certain exemplary embodiments according to the present invention, at least one of the apparatus and the implant comprises exclusively (one or more) materials that are not magnetic, ferromagnetic, or both. In some exemplary embodiments according to the present invention, at least one of the apparatus and the implant does not comprise metal or any metal alloy.

In some embodiments according to the present invention, the implant is connected or intended to be interconnected with the apparatus by means of tension threads such that the tension threads may act and/or contact the medical implant not only at one end of the medical implant but at least at two or more sections of the medical implant which are longitudinally offset from each other.

Some or all of the following advantages and the advantages mentioned above can be achieved in some, certain or all embodiments according to the present invention.

In some embodiments according to the present invention, one advantage achievable according to the present invention is to advantageously reduce or even completely avoid buckling or bulging or denting of the implant resulting from applying a force onto the implant—mainly onto the periphery thereof—by means of the tension threads.

Another advantage is a uniform folding of the implant even in a case in which an implant is designed inhomogeneously as regards the mechanical properties of the implant along the periphery thereof.

According to yet another advantage—due to the capacity of the individual shaft fibers to move, migrate or wander— the tension threads' exit from exit openings of the shaft fibers may be effected in or under angles at which the tension threads will not suffer particular friction or shear stress at the exit or shaft openings. In connection therewith, a further advantage could be that the force for folding—again due to the possibility of the individual shaft fibers to move, migrate or wander—is acting on the implant under particularly advantageous angles.

According to yet another advantage, the tension threads which pass through one or more shaft opening(s) of a particular individual shaft fiber and which also pass together through a common aperture of the implant are guided more or less in parallel between shaft opening and aperture. Further, even upon folding or unfolding of the implant, the pair of tension threads do remain parallel (or the angle between does not change or not substantially change). This way, in particular weaker stents or implants (weak being related to the force required for folding or crimping the implant) may be folded or crimped without buckling, even if only a small number of apertures is provided. Otherwise, upon folding or crimping, the implant may just buckle. With the present invention, single sections of the circumference or rim portions are compressed by forces applied onto the rim portions between the respective apertures. Hence, the force applied acts advantageously also in a circumferential direction.

In the following, the present invention will be exemplarily described with respect to the appended drawing. In the drawing, same reference numerals refer to same or identical elements. In the drawing:

FIG. 1a shows a partial longitudinal section through an apparatus of a set according to the present invention, a section of which is shown in a schematically simplified manner, prior to unfolding the implant;

FIG. 1b shows a section along the line I-I of FIG. 1a;

FIG. 2b shows a section along the line II-II of FIG. 2a;

FIG. 3b shows a section along the line III-III of FIG. 3a.

FIG. 4b shows part of what is seen in FIG. 4a; and

FIG. 5a, 5b show an implant as used in particular embodiments of the set according to the present invention.

Figure 2A:
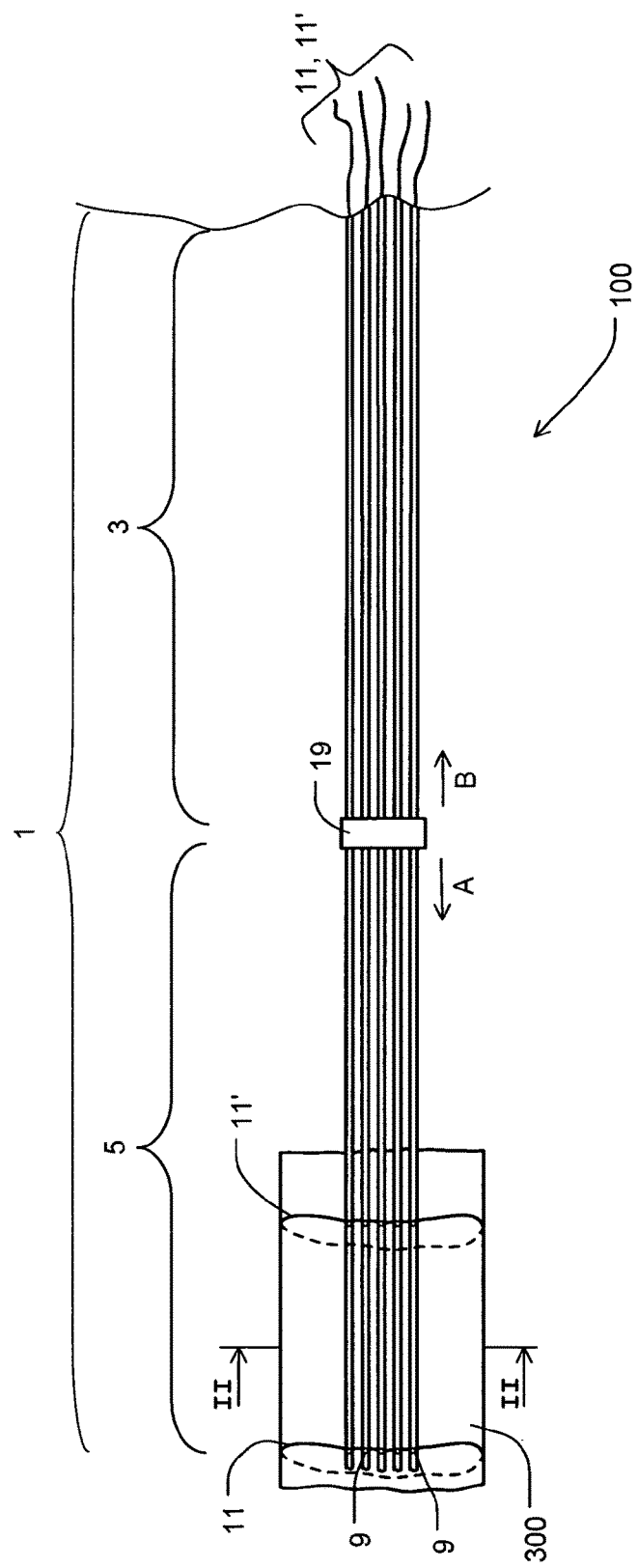
FIG. 2a shows a partial longitudinal section through the apparatus of a set according to the present invention of FIG. 1a, a section of which is shown in a schematically simplified manner, after unfolding the implant, with tension-free tension threads.

FIG. 1 shows a partial longitudinal section through an apparatus 100 of a set according to the present invention that is shown in a schematically simplified manner and only in a section thereof. The apparatus 100 comprises a shaft 1 comprising a first section 3 and a second section 5. A plurality of individual shaft fibers 13 extends along or about both the first section 3 and the second section 5. The first and the second section 3, 5 may be referred to as shaft section.

The individual shaft fibers 13 comprise shaft openings 9. Merely exemplarily, FIG. 1a shows two tension threads 11 and 11' each which exit from a shaft opening 9, twining or looping around a rim portion of the implant 300 shown in a folded state in FIG. 1a and—to be understood merely exemplarily as well—which re-enter into the same or into another shaft opening 9 of the same shaft fiber 13.

One tension thread or more tension threads 11 and 11' may exit from an interior of the shaft 1 towards the exterior of the shaft 1 through the shaft openings 9 and/or may enter in the opposite direction. In FIG. 1a, all threads 11 and 11' both exit and enter in a loop manner through the shaft openings 9.

The tension threads 11 and 11' are provided or intended to encompass an implant not shown in FIG. 1a such that the implant will have an altered diameter when altering the tension applied onto the threads 11 and 11' in sections thereof.

In the state of the implant 300 shown in FIG. 1a, the tension threads 11 and 11' are arranged at the implant 300 under tension by means of which they inhibit an undesired opening, unfolding or expansion of the implant 300 (the latter resulting, e. g., from a memory shape property of the implant).

FIG. 1a shows only two tension threads 11 and 11'. This serves for the purpose of clarity. However, a person skilled in the art will recognize that every shaft fiber 13 can comprise one or more of such tension threads. The latter can exit from the shaft fibers 13 at different heights thereof, wherein this applies both for one the same shaft fiber 13 and, e. g., adjacent shaft fibers 13.

As can be seen from FIG. 1a, the individual shaft fibers 13 arranged on the right side (i. e. away from the tip of the apparatus 100 or within the second section 5, respectively) of a device 19 for bundling individual shaft fibers 13 are combined or concentrated in a bundle. In the second section 5 (i. e. on the left side of the device 19 or towards the tip of the apparatus 100, respectively), the shaft fibers 13 are arranged freely movably—relative to each other, although, in the state of the implant 300 shown in FIG. 1a, they also contact each other—as they do also in section 5.

On the one hand, the device 19 for bundling allows for the bundled shaft fibers 13 in FIG. 1a to move freely in radial direction on the left side of the device 19. Thereby, they can follow the motion or movement or geometry of the unfolded implant 300. The device 19 is arranged not to hamper that movement.

On the other hand, the device 19 for bundling allows for setting the rigidity or stiffness of the shaft fiber 13 on the left side of the device 19. By shifting the device 19 along the shaft 1 to the left as indicated by arrow A in FIG. 1a, the rigidity or stiffness of the individual shaft fibers 13 beyond the device 19 can be increased. By shifting the device 19 in the direction indicated by arrow B (i. e. to the right side in FIG. 1a), the rigidity or stiffness of the shaft fiber 13 on the left side of the device 19 can be reduced. In this way, the apparatus 100 may advantageously be adapted to different features or behaviour of different implants.

It is obvious that the implant is represented in a very schematic and simplified manner. The present invention may be carried out with any implant designed or embodied to be foldable and/or unfoldable by means of tension threads upon implantation.

FIG. 1b shows a section along line I-I of FIG. 1a.

FIG. 2a shows a partial longitudinal section through the apparatus 100 of FIG. 1a that is shown in a schematically simplified manner and only in a section thereof after having entirely unfolded the implant 300 with the tension threads 11 and 11' being completely or substantially released or free from tension.

The individual shaft fibers 13 are present in a bundled form on both sides of the device 19 (i. e. on the left side and on the right side of the device 19, i. e. both in the first section 3 and in the second section 5). In any case they are provided in a bundle in which the individual shaft fibers 13 are close to each other or even contact each other. Due to their form which they take on while not experiencing any external tension or force, the shaft fibers 13 are present in an extended or stretched form in the second section 5. This is possible because the tension threads 11 and 11' are getting longer or stretch upon (or after) opening or unfolding of the implant 300. The latter can be achieved by correspondingly actuating the tensioning device not shown in the figures.

Figure 2B:
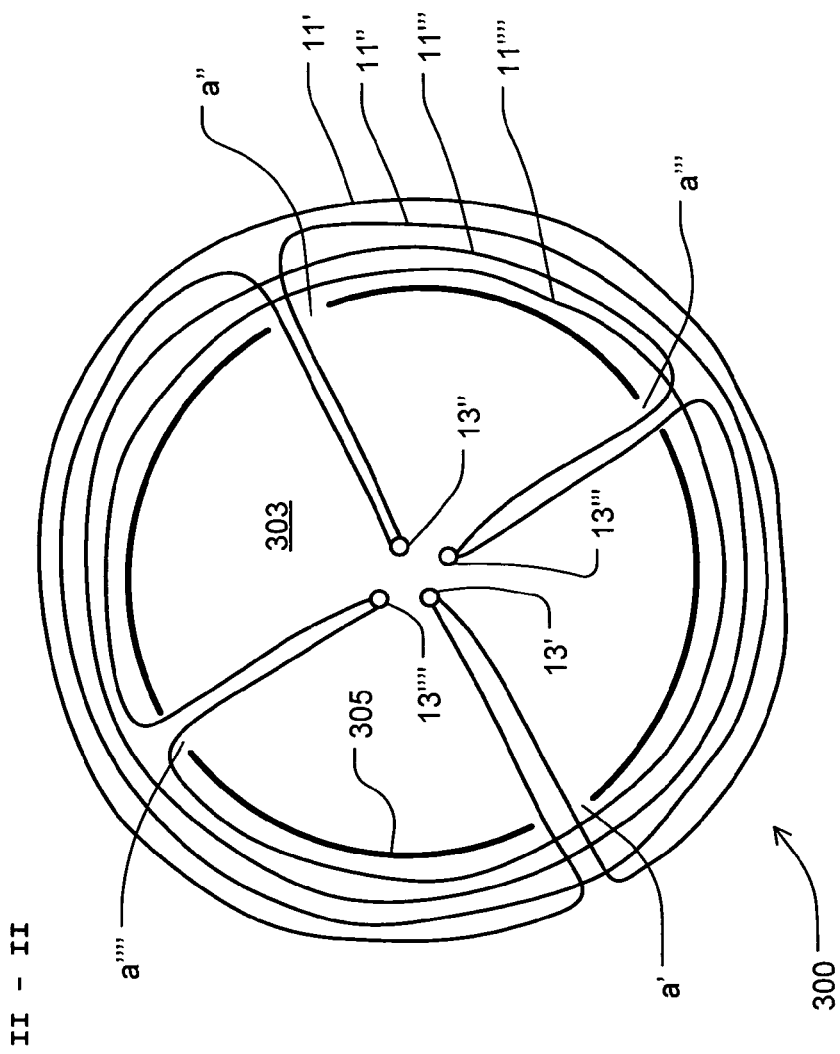

FIG. 2b shows a section along the line II-II of FIG. 2a. As can be recognized, the four individual shaft fibers 13', 13", 13'" and 13"" are present in a bundle such as shown in FIG. 1b; however, they are only bundled loosely and are not pressed against each other by an external force.

Tension threads 11', 11", 11'" and 11"" that are shown by way of example each encompass the whole circumference of the implant after having left the lumen 303 of the implant 300 through apertures a', a", a'" and a"" provided in the rim 305 thereof. In all sections of the circumference the tension threads 11', 11", 11'" and the tension thread 11"" are provided.

In other embodiments than the one shown in FIG. 2b some or all of the tension threads 11', 11", 11'" and 11"" do not encompass the whole circumference of the implant. Rather, one or more of the tension threads may re-enter the lumen 303 of the implant 300 through apertures a', a", a'" and a"" (also referred to as penetration openings herein) provided within the circumference or rim 305 of the implant 300 that are, for example, adjacent to the aperture through which the respective tension thread has exited from the lumen 303. In fact, some or all of the tension threads 11', 11", 11'" and 11"" are provided to re-enter the lumen 303 by an aperture a', a", a'" and a"" provided in the rim 305 different from the aperture through which the particular tension thread has exited. In particular, any tension thread may re-enter the lumen 303 by the next aperture, the next but one, next but two, next plus three, or the like. For example, the tension thread 11' that exits from aperture a' may re-enter again through aperture a", a'" or a"". Generally said, any tension thread that exits from an aperture or penetration opening a' may re-enter through an aperture a'+n, n comprising all natural numbers ranging from 1 (defining one of the two apertures directly neighboring aperture a') to m (m being the overall number of all apertures but one which are provided along the circumference).

Figure 3A:
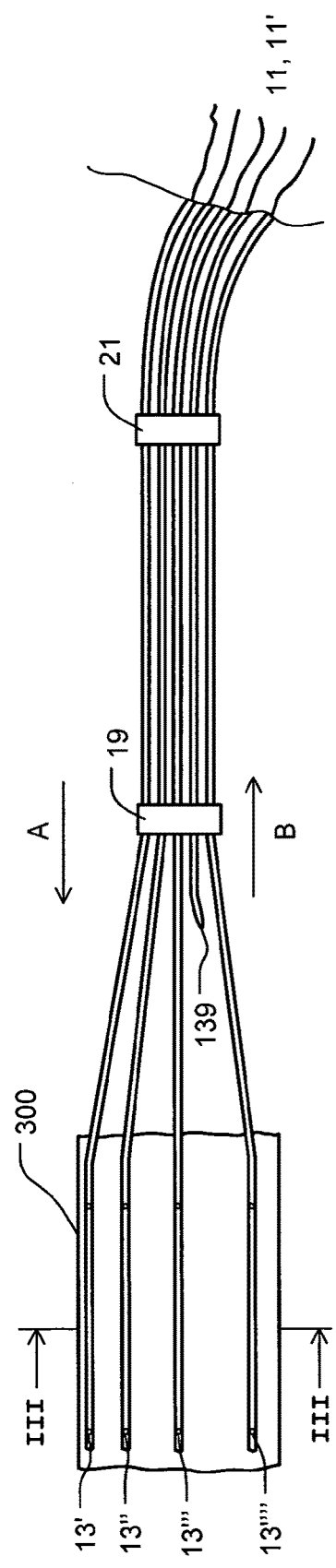
FIG. 3a shows a partial longitudinal section through the apparatus of a set according to the present invention of FIG. 1a, a section of which is shown in a schematically simplified manner, after unfolding the implant with tensioned tension threads.

FIG. 3a shows a partial longitudinal section through the apparatus 100 of FIG. 1a that is shown in a schematically simplified manner and only in a section thereof after unfolding the implant 300 using tensioned tension threads. For example, the four shaft fibers 13', 13", 13'" and 13"" are present within the implant 300. As can be seen from FIG. 3b in which an additional cut shaft fiber 139 is shown, the number of four shaft fibers is merely chosen for improved clarity and more than four shaft fibers may be present. However, a person skilled in the art will recognize the latter when considering the above specification.

Figure 3B:
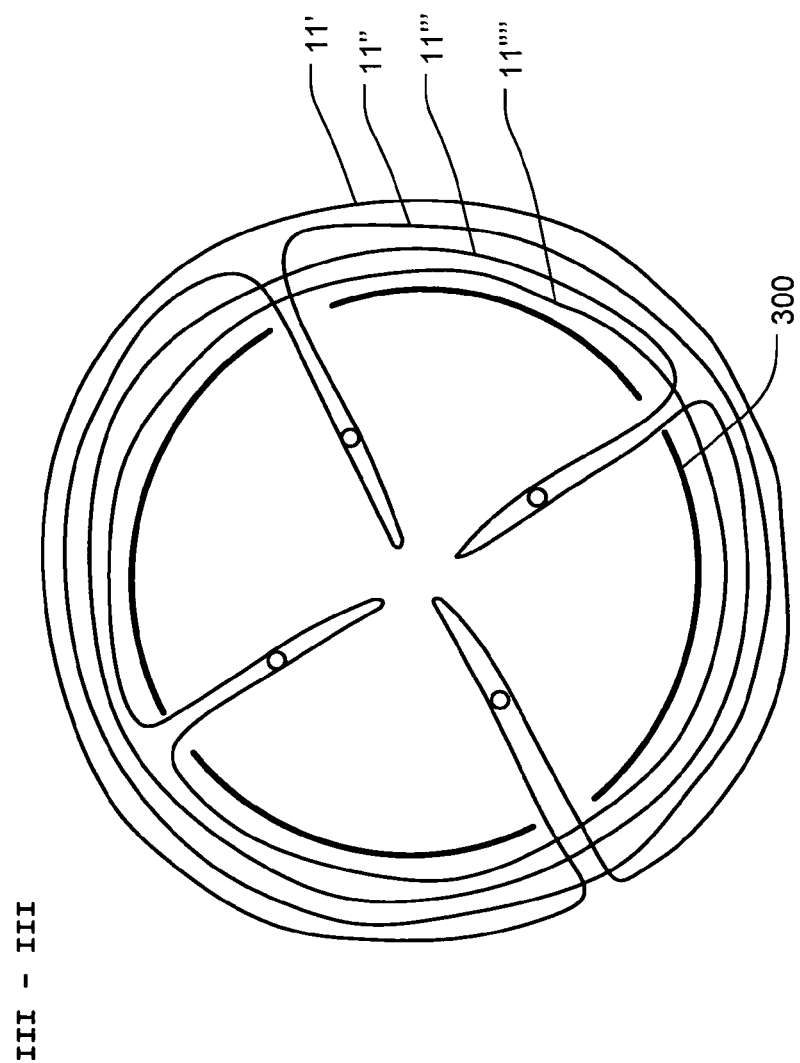

FIG. 3b shows a section along the line III-III of FIG. 3a.

It can readily be seen that, due to the tension applied by means of the respective tension threads 11', 11", 11'" and 11"", the shaft fibers 13', 13", 13'" and 13"" have moved from the center of the implant 300 towards a rim area of the implant 300 or at least in a radial direction. One effect of this motion or movement is explained in detail with respect to FIGS. 4 and 5 below.

In FIG. 3a, only by way of example, a second device for bundling depicted as reference numeral 21 is shown. As can be seen from FIG. 3a, the shaft fibers' portions situated between the two devices 19 and 21 are kept in parallel by means of the devices 19 and 21. On the right side of device 21 for bundling, the shaft fibers can flex or bend again.

Figure 4A:
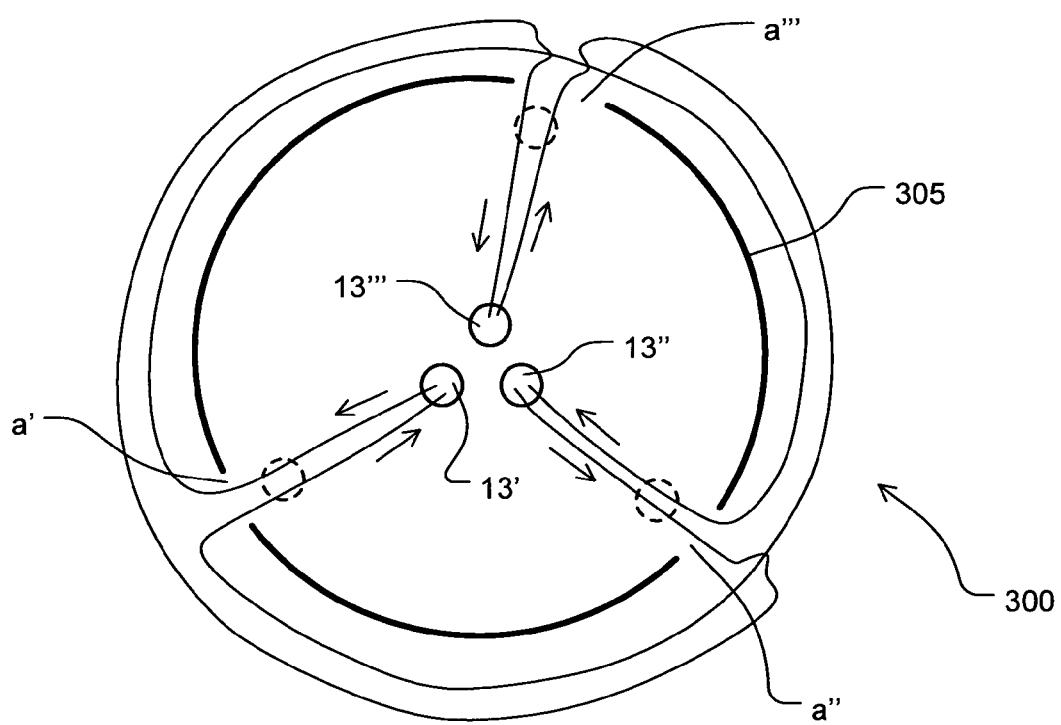
FIG. 4a shows a partial longitudinal section through the apparatus of a set according to the present invention of FIG. 1a similar to FIG. 2b, a section of which is shown in a schematically simplified manner, after unfolding the implant, with tension-free tension threads.

FIG. 4a shows a partial longitudinal section through the apparatus of a set according to the present invention in a schematically simplified manner. Again, the tension threads are shown after unfolding the implant in a tension-free state.

Figure 4B:
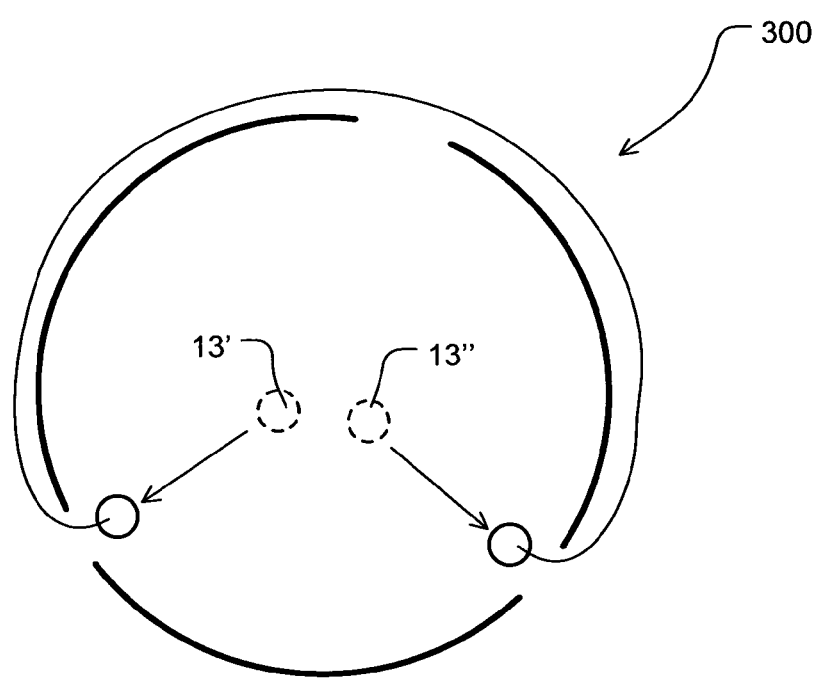

In contrast to the set shown in FIG. 2b, only three shaft fibers 13', 13" and 13'" and only three apertures a', a" and a'" are shown. Another difference between the set of FIG. 2b and the set of the FIG. 4b is that the tension threads exiting from a particular shaft fiber, e. g. shaft fiber 13', does not enter into the same shaft fiber 13' again. Rather, in the example of FIG. 4b, each fiber covers two thirds of the circumference 305 of the implant 300. That is, in the example of FIG. 4b, each pair of two tension threads extending parallel to each other between a particular shaft fiber and a common aperture of the implant's circumference do not belong to a common tension thread. A pair of two tension threads extending parallel to each other between a particular shaft fiber and a common aperture do not—with respect to what is shown in FIG. 4a—constitute start and end of one particular tension thread.

In FIG. 4a, there are possible positions of the shaft fibers 13', 13" and 13'" marked as dotted circles. Those circles are located closer to the circumference 305 the non-dotted positions in the center area of the implant 300.

As can be derived from the dotted positions which related to a non tension-free state of the tensions threads, which state is not shown in FIG. 4a, even in the non tension-free state pairs of tension threads extending parallel to each other between a particular shaft fiber and a common aperture of the implant's circumference remain parallel to each other even during folding of the implant.

The arrows shown in FIG. 4a are provided for easier reference only.

FIG. 4b shows part of what is seen in FIG. 4a. In particular, it shows only two shaft fibers 13' and 13" connected by one tension thread. Also otherwise not necessarily derivable from FIG. 4b, the position of the shaft fibers 13' and 13" indicate that the tension thread shown in FIG. 4b is not in a tension-free state. Rather, it requires some tension acting on the tension tread and via the latter on the shaft fibers to move them from the center section of the implant 300 where the shaft fibers are only indicated in dotted lines towards the circumference 305 as shown in FIG. 4b.

FIG. 5a shows an exemplary implant 300 as used in particular embodiments of the set according to the present invention in an unfolded state, FIG. 5b in a more folded condition.

As can be seen from FIGS. 5a and 5b, the implant 300 has a first structural element embodied as proximal ring 307 and a second structural element embodied as distal ring 309 as described supra.

The proximal ring 307 and the distal ring 309 are interconnected with each other by means of three (could be more or less) interconnecting elements which are embodied in the implant 300 of FIGS. 5a and 5b by way of example as posts or struts 312.

As can further be seen from FIGS. 5a and 5b, the posts 312 each comprise (at least) two circular apertures a (which may have any other shape such as elliptic, oval, rectangular, and the like), through which strings or threads 11 are routed from an inner space of the implant 300 of the centre in which the tips of the individual shaft fibers (not shown in FIGS. 5a and 5b) are placed to an outside of the implant 300 for controlling the expansion and re-folding of the implant 300 as is explained in great detail in WO 2008/029296 A2 ("Minimally invasive heart valve replacement", filed on Feb. 15, 2007) to the inventors of the present invention. For further general details on the implant and the catheter it is referred to that document, the respective disclosure of which is herewith incorporated by way of reference.

Posts 312 comprise a number of apertures 314, exemplarily arranged in two parallel rows extending in a longitudinal direction of the implant 300. As is explained in WO 2008/029296 A2 in detail, the apertures 314 may be used for passing chords or ties through the posts 312 to secure lateral edges of leaflets or the like in place with the interior of the implant 300 to create a working valve, for example. It has to be noted that according to the present invention, one row of apertures 314 (of any shape and size thereof) is also contemplated. Having one row instead of two rows advantageously allows for designing posts having a smaller width. A smaller width of the post 312 allows in turn that the implant can be designed to be more open, even more flexible, that more space is left for the functionally effective part of the implant and the like.

FIGS. 5a and 5b show how one particular embodiment of the implant according to the invention may look like seen from the side. It is, however, to be noted that due to the perspective chosen, FIGS. 5a, 5b do not show the particularities of the present invention. Those can be seen from, e. g. FIGS. 2b to 4b.

The invention claimed is:

1. A set comprising:
an apparatus for folding or unfolding at least one medical implant by means of at least one tension thread; and
at least one foldable and/or unfoldable implant connected with tension threads for the purpose of folding and/or unfolding of the implant or provided or prepared for being connected with tension threads;
wherein the apparatus comprises:
a shaft;
a tensioning device for altering a form or shape of the foldable and/or unfoldable implant by means of the tension thread; and
wherein the shaft comprises in at least one shaft section thereof a plurality of individual shaft fibers;
the individual shaft fibers have each at least one shaft opening for passing through the tension threads;
wherein the implant comprises:
apertures through which tension threads are guided;
and wherein each of the tension threads exits from the respective shaft fiber, continues to attach to the implant, and re-enters into the same or another shaft fiber, and tension threads which pass through one or more shaft opening(s) of a particular individual shaft fiber also pass together through a same aperture of the implant and are guided in parallel or substantially in parallel between the individual shaft fiber and the implant in at least one direction or in one plane perpendicular to a longitudinal axis of the implant.

2. The set according to claim 1, wherein, during use of the apparatus, shaft fibers of the plurality of individual shaft fibers are always present in bundled form in at least one first section of the shaft section, whereas, in a second section, the shaft fibers are provided or intended for moving away from each other during use of the apparatus.

3. The set according to claim 2, wherein shaft fibers of the plurality of individual shaft fibers each comprise one or more shaft openings by means of which the one or more tension threads can exit from and/or enter into the respective shaft fiber.

4. The set according to claim 2, wherein, during a state of use of the apparatus, shaft fibers of the plurality of individual shaft fibers are arranged movably in or from at least the second section of the shaft independently of each other and/or independently of the position of the implant relative to the apparatus for folding or unfolding of the implant.

5. The set according to claim 2, wherein the shaft comprises in at least one section thereof at least one device for bundling individual shaft fibers of the plurality of individual shaft fibers.

6. The set according to claim 2, wherein individual shaft fibers are designed or embodied and intended or provided for moving towards a rim portion of the implant when applying tension onto the implant by means of the tension threads extending through these individual shaft fibers.

7. The set according to claim 2, wherein tension threads exiting from individual shaft fibers are connected with a rim portion of the implant for applying a force onto the rim portion, wherein the rim portion only comprises the entire circumference of a foldable and/or unfoldable periphery of the implant.

8. The set according to claim 2, wherein tension threads exiting from individual shaft fibers are connected with a rim portion for applying a force onto the rim portion of the implant, in particular wherein tension threads exiting from at least two individual shaft fibers are connected with the rim portion or parts thereof.

9. The set according to claim 2, wherein individual shaft fibers and the implant are adapted such that, during a process of folding the implant, a first force required for moving the shaft fibers in a section thereof, in particular in a section comprising shaft openings for tensions threads, from their longitudinal alignment or for moving them in a direction of radial extension of the implant, is lower than a second force required for effecting folding of the implant by means of the tension threads connected with the implant and which exit from the shaft openings.

10. The set according to claim 1, wherein shaft fibers of the plurality of individual shaft fibers each comprise one or more shaft openings by means of which the one or more tension threads can exit from and/or enter into the respective shaft fiber.

11. The set according to claim 10, wherein, during a state of use of the apparatus, shaft fibers of the plurality of individual shaft fibers are arranged movably in or from at least the second section of the shaft independently of each other and/or independently of the position of the implant relative to the apparatus for folding or unfolding of the implant.

12. The set according to claim 1, wherein, during a state of use of the apparatus, shaft fibers of the plurality of individual shaft fibers are arranged movably in or from at least the second section of the shaft independently of each other and/or independently of the position of the implant relative to the apparatus for folding or unfolding of the implant.

13. The set according to claim 1, wherein the shaft comprises in at least one section thereof at least one device for bundling individual shaft fibers of the plurality of individual shaft fibers.

14. The set according to claim 13, wherein the at least one device for bundling individual shaft fibers is arranged to be shiftable or movable along a longitudinal extension of the apparatus or is otherwise alterable or manipulatable or engineerable and/or is provided or intended for being used at or on different sections of the apparatus along the longitudinal extension thereof.

15. The set according to claim 1, wherein individual shaft fibers are designed or embodied and intended or provided for moving towards a rim portion of the implant when applying tension onto the implant by means of the tension threads extending through these individual shaft fibers.

16. The set according to claim 1, wherein tension threads exiting from individual shaft fibers are connected with a rim portion of the implant for applying a force onto the rim portion, in particular wherein the rim portion only comprises the entire circumference of a foldable and/or unfoldable periphery of the implant.

17. The set according to claim 1, wherein tension threads exiting from individual shaft fibers are connected with a rim portion for applying a force onto the rim portion of the implant, in particular wherein tension threads exiting from at least two individual shaft fibers are connected with the rim portion or parts thereof.

18. The set according to claim 1, wherein the apparatus is designed or embodied as a catheter or a heart catheter, or comprises a catheter.

19. The set according to claim 1, wherein the implant is a stent or a heart valve arrangement.

20. The set according to claim 1, wherein individual shaft fibers and the implant are adapted such that, during a process of folding the implant, a first force required for moving the shaft fibers in a section thereof, in particular in a section comprising shaft openings for tensions threads, from their longitudinal alignment or for moving them in a direction of radial extension of the implant, is lower than a second force required for effecting folding of the implant by means of the tension threads connected with the implant and which exit from the shaft openings.

* * * * *